(12) United States Patent
Hartmann et al.

(10) Patent No.: US 6,297,282 B1
(45) Date of Patent: Oct. 2, 2001

(54) SUBSTITUTED DERIVATIVES OF BENZOSULPHONAMIDES AS INHIBITORS OF THE ENZYME CYCLOOXYGENASE II

(75) Inventors: Michael Hartmann, Linz; Peter Kremminger, Kufstein; Heinz Blaschke, Linz; Dagmar Stimmeder, Linz; Harald Fellier, Linz; Franz Rovenszky, Linz, all of (AT)

(73) Assignee: Nycomed Austria GmbH, Linz (AT)

( * ) Notice: Subject to any disclaimer, the term of this patent is extended or adjusted under 35 U.S.C. 154(b) by 0 days.

(21) Appl. No.: 09/355,722

(22) PCT Filed: Feb. 3, 1998

(86) PCT No.: PCT/GB98/00342

§ 371 Date: Oct. 26, 1999

§ 102(e) Date: Oct. 26, 1999

(87) PCT Pub. No.: WO98/33769

PCT Pub. Date: Aug. 6, 1998

(30) Foreign Application Priority Data

Feb. 3, 1997 (AT) ........................................... 165/97

(51) Int. Cl.$^7$ ......................... A61K 31/44; A61K 31/38; A61K 31/18
(52) U.S. Cl. ......................... 514/603; 514/347; 514/445; 546/338; 549/65; 564/82

(58) Field of Search .............................. 564/82; 546/338; 549/65; 514/347, 445, 603

(56) References Cited

U.S. PATENT DOCUMENTS 6,146,615 * 11/2000 Davies et al. ........................ 424/9.36

* cited by examiner

Primary Examiner—Peter O'Sullivan
(74) Attorney, Agent, or Firm—Wenderoth, Lind & Ponack, LLP

(57) ABSTRACT

The present application relates to compounds of formula (I) wherein A represents oxygen, sulfur or —NH—, m is 0–2, and $R_1$, $R_2$, $R_3$, $R_6$ and $R_7$ have the meanings given in the specification, to a process for their preparation, as well as to their use in the inhibition of cyclooxygenase II.

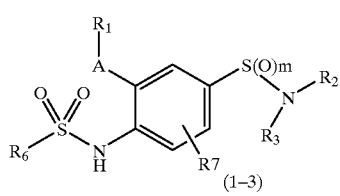

(I)

8 Claims, No Drawings

SUBSTITUTED DERIVATIVES OF BENZOSULPHONAMIDES AS INHIBITORS OF THE ENZYME CYCLOOXYGENASE II

This application is a 371 of PCT/GB98/00392 filed Feb. 3, 1998.

The invention relates to novel compounds having anti-inflammatory activity.

Prostaglandins play a decisive role in inflammatory processes and inhibition of the formation of prostaglandin, especially the formation of $PGG_2$, $PGH_2$ and $PGE_2$, is the common characteristic of compounds with anti-inflammatory activity. The known non-steroidal anti-inflammatory drugs (NSAIDs), which reduce prostaglandin-induced pain and swelling during the inflammation process, also influence prostaglandin-regulated processes which do not accompany inflammation processes. For this reason, most known NSAIDs cause undesirable side-effects in high doses, often even dangerous ulcers, especially stomach ulcers, gastric haemorrhages and such like. For this reason, the therapeutic potential of these compounds is decisively reduced.

Most known NSAIDs prevent the formation of prostaglandins by the inhibition of enzymes in human arachidonic acid metabolism, especially by inhibiting the enzyme cyclooxygenase (COX). The enzyme cyclooxygenase II (COX-2) is an enzyme of human arachidonic acid metabolism which has only been discovered recently. (Proc. Natl. Acad. Sci. USA, 89, 7384, 1992). COX-2 is induced by cytokines or endotoxins.

The discovery of this inducible enzyme, which plays a decisive role in inflammation processes, offers the possibility of searching for selectively effective compounds with an anti-inflammatory activity, which inhibit the inflammation process in a more effective manner without influencing other prostaglandin-regulated processes, and thus having fewer and fewer serious side-effects.

5-methylsulphonamide-1-indanones, which inhibit the enzyme cyclooxygenase II and which can therefore be utilised during the treatment of inflammation processes, are known from WO 94/13635. The potential of these compounds, and their side-effects, have not yet been fully clarified. Furthermore, these known compounds dissolve poorly, and thus have decisive disadvantages with regard to their formulation and application. Hence there is still a demand for new cyclooxygenase II-selective compounds, which, due to their effect and side-effect profiles, are safe and efficient in applications for the treatment of inflammatory processes.

The objective of the present invention was thus the provision of new non-steroidal anti-inflammatory drugs (NSAIDs), which selectively inhibit cyclooxygenase II (COX-2) and thus have fewer and fewer serious undesired side effects.

This objective could be unexpectedly solved by the provision of new derivatives of benzenesulphonic acid. As a result of their selective effect on the enzyme Cyclooxygenase II, these new compounds have excellent anti-inflammatory, analgesic, antipyretic and anti-allergic effects, but without the extremely undesirable side-effects of known anti-inflammatory agents.

The subject matter of the invention are thus compounds of formula I

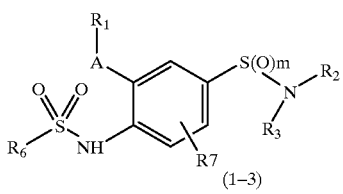

wherein
A denotes oxygen, sulphur or NH,
$R_1$ is an optionally unsaturated alkyl or alkyloxyalkyl group, optionally mono- or polysubstituted or mixed substituted by halogen, alkoxy, oxo or cyano, a cycloalkyl, aryl or heteroaryl group optionally mono- or polysubstituted or mixed substituted by halogen, alkyl, $CF_3$, cyano or alkoxy,
$R_2$ and $R_3$, independently from one another, denote hydrogen, an optionally polyfluorised alkyl group, an aralkyl, aryl or heteroaryl group or a group $(CH_2)_n$—X, or
$R_2$ and $R_3$, together with the N- atom denotes a 3 to 7-membered, saturated, partially or completely unsaturated heterocycle with one or more heteroatoms N, O or S, which can optionally be substituted by oxo, an alkyl, alkylaryl or aryl group, or a group $(CH_2)_n$—X,
X denotes halogen, $NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —$NHC(O)R_4$, —$NHS(O)_2R_4$,
n denotes a whole number from 0 to 6,
$R_6$ denotes a straight-chained or branched alkyl group with 1–10 C- atoms, a cycloalkyl group, an alkylcarboxyl group, an aryl group, aralkyl group, a heteroaryl or heteroaralkyl group which can optionally be mono- or polysubstituted or mixed substituted by halogen or alkoxy,
$R_7$ denotes halogen, hydroxy, a straight-chained or branched alkyl, alkoxy, acyloxy or alkyloxycarbonyl group with 1–6 C- atoms, which can optionally be mono- or polysubstituted by halogen, $NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —$NHC(O)R_4$, —$NHS(O)_2R_4$, or a polyfluoroalkyl group,
$R_4$ and $R_5$, independently from one another, denote hydrogen, alkyl, aralkyl or aryl, and
m denotes a whole number from 0 to 2, and the pharmaceutically-acceptable salts thereof.
A denotes oxygen, sulphur or NH.
$R_1$ denotes an optionally unsaturated alkyl or alkyloxyalkyl group, each with 1–12 C-atoms in the alkyl chain, for example a methyl, an ethyl, a propyl, an isopropyl, a butyl, an isobutyl, a tertiary-butyl, a pentyl, an isopentyl, a hexyl or an isohexyl group and the like, or for example unsaturated alkyl groups such as ethenyl, butenyl, or alkyoxyalkyl groups such as methoxymethyl, ethoxymethyl and the like. These groups can optionally be substituted by halogen, for example F, Cl or Br, by alkoxy, oxo or cyano. Furthermore, $R_1$ can denote a cycloalkyl group, for example a cyclohexyl or a cyclopentyl group, an aryl group, for example a phenyl group, or heteroaryl group, for example a furyl, thienyl, thiazolyl, imidazolyl, thiadiazolyl, pyridyl, pyridinyl or pyrazolyl group. These groups can optionally be mono- or polysubstituted or mixed substituted by halogen, for example Cl, F, Br or by $CF_3$ or alkyl with 1–4 C-atoms, for example methyl, ethyl, propyl, isopropyl, butyl, isobutyl or tertiary-butyl or alkoxy with 1–4 C-atoms, for example methoxy, ethoxy, propoxy or butoxy or cyano.

$R_2$ and $R_3$, independently from one another, denote hydrogen, an optionally polyfluorized alkyl group with 1–6 C-atoms, for example methyl, an ethyl, a propyl, an isopropyl, a butyl, an isobutyl, a tertiary-butyl, a pentyl, an isopentyl, a hexyl or an isohexyl group, a $CF_3$ group or $C_2F_5$, an aralkyl group with 1–4 C-atoms in the alkyl chain, for example a benzyl group, an ethylphenyl group, an aryl group, for example a phenyl group or a heteroaryl group, for example a pyridyl group, a pyridazinyl group, a thienyl group, a thiazolyl group or an isothiazolyl group.

$R_2$ and $R_3$ can also, independently from one another, denote a group —$(CH_2)_n$—X, whereby X is halogen, —$NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —$NHC(O)R_4$, —$NHS(O)_2R_4$, and n is a whole number from 0 to 6.

Examples of such groups are halogen alkyl groups, for example chloromethyl, chloroethyl, the group —CN, nitroalkyl groups, for example nitromethyl, nitroethyl or cyanoalkyl groups, for example cyanomethyl, cyanopropyl, cyanohexyl, a hydroxy group or hydroxyalkyl groups, for example hydroxymethyl, hydroxyethyl, hydroxypropyl bishydroxymethyl-methyl. Other examples are alkoxy groups such as methoxy, ethoxy, propoxy, butoxy, pentoxy, the groups methyloxy-ethyl, ethyloxy-methyl, carboxylic acid groups such as ethoxycarbonyl, methoxycarbonyl, acetyl, propionyl, butyryl, isobutyryl groups and their alkyl-, aralkyl- or aryl esters, carbamoyl groups, oxycarbonyloxy groups, for example the ethoxycarbonyloxy group, carboxymide acid groups, thiocarboxy groups and such like.

$R_4$ and $R_5$ denote, independently of one another, hydrogen, alkyl with 1–6 C-atoms, aralkyl with 1–4 C-atoms in the alkyl chain, for example benzyl, ethylphenyl or aryl, for example phenyl.

Furthermore, $R_2$ and $R_3$, together with the N-atom, can form a 3- to 7-membered, saturated, partially or completely unsaturated heterocycle with one or more heteroatoms N, O or S, which may optionally be substituted by oxo, an alkyl, alkylaryl or aryl group or a group —$(CH_2)_n$—X, whereby X denotes halogen, $NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —$NHC(O)R_4$, —$NHS(O)_2R_4$, and n is a whole number from 0 to 6.

Examples of such rings are the morpholyl group, the aziridinyl group, the azetidinyl group, the pyridyl group, the pyrazolyl group, the thiazolyl group and such like.

$R_6$ denotes a straight chain or branched alkyl group with 1–10 C-atoms, for example methyl, an ethyl, a propyl, an isopropyl, a butyl, an isobutyl, a tertiary-butyl, a pentyl, an isopentyl, a hexyl or an isohexyl group or such like, a $CF_3$ group or $C_2F_5$, an aralkyl group with 1–4 C-atoms in the alkyl chain, for example a benzyl group, an ethylphenyl group, an aryl group, for example a phenyl group or a heteroaryl group, for example a pyridyl group, a pyridazinyl group, a thienyl group, a thiazolyl group or an isothiazolyl group or a heteroaralkyl group, for example. These groups can, for example, be mono- or polysubstituted or mixed substituted by halogen, for example Cl, F or Br, or alkoxy, for example methoxy, ethoxy and such like, by —$NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —$NHC(O)R_4$, —$NHS(O)_2R_4$.

The compounds, according to the invention, can be prepared by reacting a compound of formula III

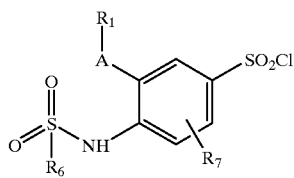

III with a compound of formula IV $HNR_2R_3$            IV or a salt thereof.

This reaction preferably takes place in the presence of a diluent or solvent which is inert under reaction conditions, for example dioxan, tetrahydrofuran or such like. The reaction temperature is approximately −10° C. up to the reflux temperature of the solvent or diluent preferably −10° C. up to room temperature.

The starting compounds of formula III can, for example, be prepared according to the following reaction scheme or by other methods familiar to the skilled person.

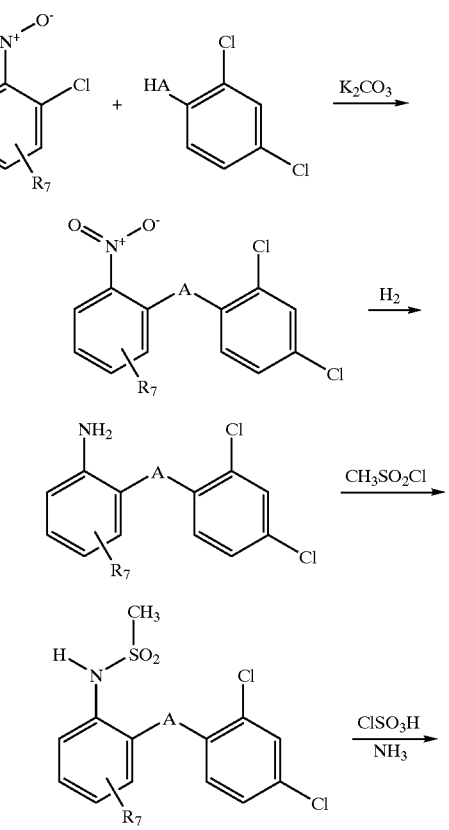

-continued

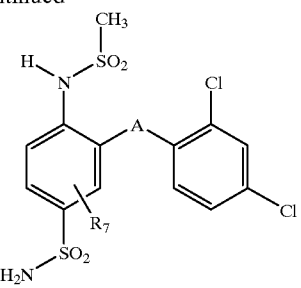

The compounds of formula I, obtained as described above, are acidic or basic compounds and can be converted in the usual manner with inorganic or organic bases or acids respectively into their pharmaceutically-acceptable salts. The salt formation can, for example, be carried out by adding at least an equivalent quantity of the desired base or acid to a compound of formula I in a suitable solvent, such as for example water, acetone, acetonitrile, benzene, dimethylformamide, dimethyl-sulphoxide, chloroform, dioxan, methanol, ethanol, hexanol, ethylacetate, or in an aliphatic ether, for example diethylether, or mixtures of such solvents, being mixed well, and after completion of salt formation the precipitated salt is filtered off, lyophilised or the solvent is distilled off in a vacuum. If necessary, the salts can be recrystallised after isolation.

Pharmaceutically-acceptable salts are those with inorganic acids, such as for example hydrochloric acid, hydrobromic acid, sulphuric acid, phosphoric acid or nitric acid, or with organic acids such as citric acid, tartaric acid, maleic acid, fumaric acid, succinic acid, malic acid, methanesulphonic acid, aminosulphonic acid, acetic acid, benzoic acid and such like.

Pharmaceutically-acceptable salts are e.g. metallic salts, especially alkaline metal or alkaline-earth metal salts such as sodium, potassium, magnesium or calcium salts. Other pharmaceutical salts are, for example, easily-crystallising ammonium salts. These are derived from ammonia or organic amines, such as mono-, di- or tri-lower-(alkyl, cycloalkyl or hydroxyalkyl)-amines, lower alkylene diamines or hydroxy- or aryl-lower-alkyl ammonium bases e.g. methylamine, diethylamine, triethylamine, ethylenediamine, tris-(hydroxymethyl)-aminomethane, benzyltrimethylammonium hydroxide and such like.

The new compounds have good solubility and, as a result of their selective effect on the enzyme cyclooxygenase II, they have excellent anti-inflammatory, analgesic, antipyretic and antiallergic effects, but without the extremely undesirable side-effects of known anti-inflammatory agents.

As a result of this pharmacological characteristic, the new compounds can be used, individually or in combination with other effective substances in the form of common galenic preparations as medicaments for the treatment of disorders or diseases which can be treated or healed by inhibition of the enzyme cyclooxygenase II.

These disorders or diseases embrace pain, fever and inflammations of various types, for example rheumatic fever, symptoms associated with influenza or other viral infections, head and joint pains, toothache, sprains, distortions, neuralgia, muscle inflammation, joint inflammation, joint membrane inflammation, arthritis, rheumatoid arthritis, other rheumatic inflammation form degenerative manifestations, for example osteoarthritis, gouty arthritis, stiffening of the joints, spondylitis, bursitis, burns and injuries.

The invention thus relates to pharmaceutical preparations which contain the compounds of formula I, according to the invention, or their salts, alone or mixed with other therapeutically-active substances, as well as common galenic adjuvant and/or carrier substances or diluents.

The compounds according to the invention can be orally applied in the form of tablets or capsules which contain a single dose of the compound together with adjuvant substances and diluents such as maize starch, calcium carbonate, dicalcium phosphate, algenic acid, lactose, magnesium stearate, primogel or talcum. The tablets are manufactured in the traditional manner by granulating the contents and pressing into shape, the capsules by filling hard gelatine capsules of suitable size.

A further application form of the compounds, according to the invention, are suppositories which contain adjuvant substances such as beeswax derivatives, polyethylene glycol or polyethylene glycol derivatives, linoleic acid or linoleic acid esters, together with a single dose of the compound and which are rectally administered.

The compounds, according to the invention, can also be parenterally applied, for example by intramuscular, intravenous or subcutaneous injection. For parenteral application, it is best that they are used in the form of a sterile aqueous solution, which can contain other dissolved materials such as tonic agents, agents for standardization of the pH value, preservatives and stabilisers. Distilled water can be added to the compounds and the pH value can be adjusted to between 3 and 6 by using, for example, citric acid, lactic acid or hydrochloric acid. Sufficiently-dissolved materials, such as dextrose or salt solutions, can be added in order to isotonically set the solution. In addition, preservatives such as p-hydroxybenzoate, and stabilisers such as EDTA, can be added to give the solution a sufficient shelf-life and stability. The solution obtained in this way can then be sterilised and decanted into sterile ampoules of a suitable size so that they contain the desired volume of solution. The compounds, according to the invention, can also be applied by infusion of a parenteral formulation as described above.

Furthermore, the compounds, according to the invention, can be formulated for topical or transdermal application with suitable adjuvant and/or carrier substances, emulsifiers, tensides and/or diluents, e.g. vaseline, olive oil, peanut oil, sesame seed oil, soya oil, water, glycols, cetylstearyl esters, triglycerides, cetaceum, miglyol and such like into ointments, creams, gels or plasters, or for example formulated into powder with talcum.

For oral application with humans, it is accepted that the daily dosage of a compound according to the invention, will lie in the range of 0.01 to 1000 mg per day for a typical adult patient of 70 kg. Hence tablets or capsules can usually contain 0.003 to 300 mg of active compound, for example 0.1 to 50 mg, for oral application up to three times per day. With parenteral administration, the dose can lie in the range of 0.001 to 1000 mg per 70 kg per day, for example approximately 5 mg.

Example 1

3-(2,4-Dichlorophenylthio)-2-chloro-4-methylsulphonylamino-benzosulphonamide $C_{13}H_{11}Cl_3N_2O_4S_3$ FW: 461.79 gmol$^{-1}$

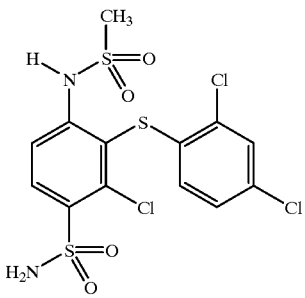

a) 3-chloro-2-(2,4-dichlorophenylthio)-nitrobenzene

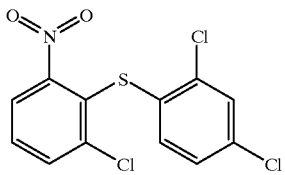

Sodium carbonate (13.8 g) is added to a solution of 1,2-dichloro-3-nitrobenzene (19.29 g) and 2,4-dichlorothiophenol (17.9 g) in xylene (250 ml), and the resulting mixture is heated for 5 hours at reflux temperature. The precipitate is separated by filtration, washed with xylene and the combined organic phases are concentrated. The resultant residue is mixed with petroleum ether and stirred for 1 hour at room temperature. Following this, the crystalline material is suction filtered and washed with petroleum ether, and any remaining solvent is removed in a vacuum. Yield: 25.6 g of colourless crystals (76.6%).

b) 3-chloro-2-(2,4-dichlorophenylthio)-aniline

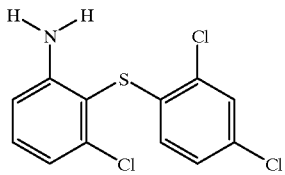

A solution of 3-chloro-2-(2,4-dichlorophenylthio)-nitrobenzene (10.04 g) in dioxan (100 ml) is mixed with Raney-nickel (5 g). Following this, the mixture is shaken for 3 hours at room temperature and 3 bar hydrogen pressure in a Parr apparatus. The catalyst is removed by filtration. The filtrate is concentrated in a vacuum and the resulting residue is brought to constant weight in a vacuum. Yield 9.01 g (98.6%) of colourless oil.

$^{13}$C-NMR (CDCl$_3$, 100 MHz): δ151.1, 141.4, 133.4, 131.9, 131.8, 131.3, 129.3, 127.5, 126.6, 119.4, 113.5, 111.2.

c) 3-chloro-2-(2,4-dichlorophenylthio)-N-methyl-sulphonyl-aniline

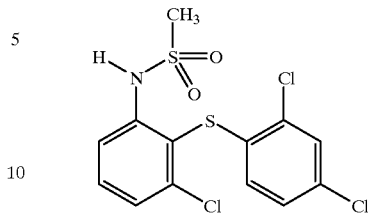

3-chloro-2-(2,4-dichlorophenylthio)-aniline (8.96 g) is dissolved in pyridine (300 ml). Methane sulphochloride (4.56 ml) is added dropwise to this solution and the resulting mixture is stirred for 12 hours at room temperature. Following this, the mixture is emptied onto iced water, acidified with concentrated hydrochloric acid. The resulting mixture is extracted 3 times with methylene chloride (each 200 ml). The combined organic phases are dried (Na$_2$SO$_4$), filtered and the filtrate is concentrated in a vacuum. The resulting residue is dissolved in methanol, mixed with a sodium methylate solution in methanol (29.7%, 50 ml) and is stirred for 12 hours. The clear solution is acidified with concentrated hydrochloric acid, brought to room temperature, diluted with water (200 ml). The result in precipitate is suction filtered, washed with water and dried. Yield: 10.69 g (95.0%).

$^{13}$C-NMR (CDCl$_3$, 100 MHz): δ142.1, 142.0, 132.8, 132.63, 132.58, 131.8, 129.9, 127.9, 127.4, 125.9, 118.4, 116.9, 40.0.

d) 2-chloro-3-(2,4-dichlorophenylthio)-4-methylsulphonylamino-benzosulphonamide

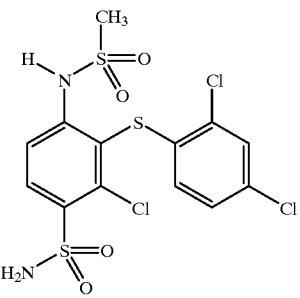

Chlorosulphonic acid (3.69 ml) is dissolved in methylene chloride (100 ml), cooled to 0° C. and added dropwise to a solution of 3-chloro-2-(2,4-dichlorophenylthio)-N-methylsulphonyl-aniline (10.69) in methylene chloride (100 ml). After an hour, phosphorus pentachloride (23.07 g) is added and the mixture is stirred for one more hour at 0° C. Following this, the solution is brought to room temperature and stirred for a further one hour. The precipitate is suction-filtered and the filtrate is emptied onto an iced water mixture. The organic phase is separated, dried (Na$_2$SO$_4$), filtered and concentrated in a vacuum. The resulting residue is dissolved in dioxan (80 ml) and is added dropwise to a mixture of dioxan (80 ml) and concentrated aqueous ammonia (120 ml), cooled to 0° C. The resulting mixture is stirred for a further 2 hours at room temperature. Following t his, it is diluted with water (250 ml), acidified with concentrated hydrochloric acid and cooled to room temperature. The resulting crystals are suction-filtered, washed with ethanol and dried in a vacuum. Yield: 6.74 g (59.0%).

$^{13}$C-NMR (d$_6$-DMSO, 100 MHz): δ145.5, 138.7, 133.5, 131.8, 131.1, 131.1, 129.3, 128.3, 127.5, 123.5, 120.4, 41.4.

The following compounds were prepared analogously to Example 1:

Example 2

5-(2.4-dichlorophenylthio)-2-methyl-4-methylsulphonylamino-benzosulphonamide

C$_{14}$H$_{14}$Cl$_2$N$_2$O$_4$S$_3$

FW: 441.38 gmol$^{-1}$

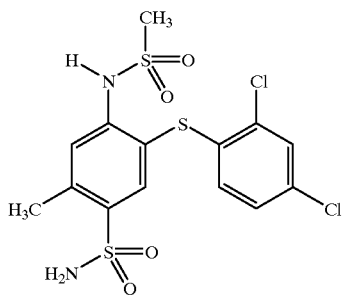

mp: 250–253° C.

$^{13}$C-NMR (d$_6$-DMSO, 100 MHz): δ153.8, 138.2, 137.8, 137.3, 134.0, 130.1, 129.0, 128.6, 128.2, 127.0, 120.5, 113.2, 41.0, 20.8.

Example 3

5-(2,4-dichlorophenylthio)-2-methoxy-4-methylsulphonylamino-benzosulphonamide

C$_{14}$H$_{14}$Cl$_2$N$_2$O$_5$S$_3$

FW: 457.38 gmol$^{-1}$

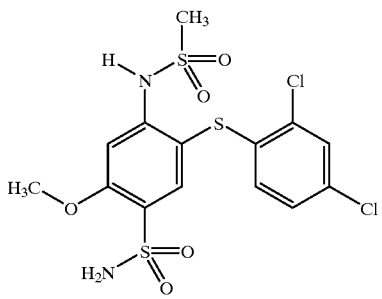

Mp: 258–262° C.

$^{13}$C-NMR (d$_6$-DMSO, 100 MHz): δ158.2, 145.2, 136.2, 135.4, 131.3, 131.1, 129.3, 128.8, 128.3, 11.3, 106.4, 56.6, 41.0.

Example 4

5-(2,4-dichlorophenylthio)-2-hydroxy-4-vinyl sulphonylamino-benzosulphonamide

C$_{13}$H$_{12}$Cl$_2$N$_2$O$_4$S$_3$

FW: 443.35 gmol$^{-1}$

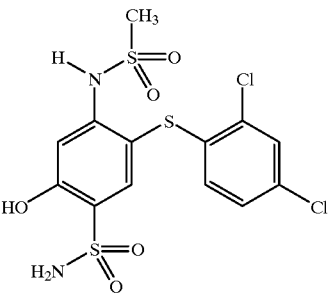

$^{13}$C-NMR (d$_6$-DMSO, 100 MHz): δ157.6, 145.0, 137.0, 135.9, 130.9, 130.8, 129.2, 128.3, 128.0, 127.2, 109.6, 108.7, 56.2, 18.7.

Example 5

5-(2,4-dichlorophenylthio)-2-hydroxymethyl-4-methylsulphonylamino-benzosulphonamide C$_{14}$H$_{14}$Cl$_2$N$_2$O$_5$S$_3$ FW: 457.38 gmol$^{-1}$

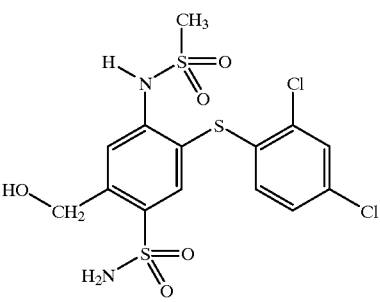

Mp: 185–187° C.

$^{13}$C-NMR (d$_6$-DMSO, 100 MHz): δ138.0, 136.6, 135.5, 134.3, 133.7, 133.2, 130.9, 129.5, 128.6, 128.3, 128.2, 127.2, 35 41.1, 34.3.

Example 6

3-(2,4-dichlorophenylthio)-4-vinylsulphonyl-amino-benzosulphonamide $C_{14}H_{12}Cl_2N_2O_4S_3$ FW: 439.36 gmol$^{-1}$

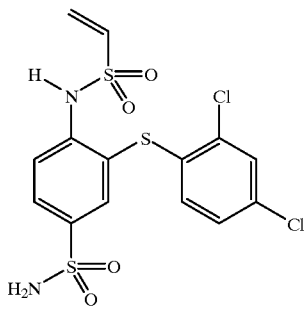

Mp: 180–182° C.

$^{13}$C-NMR (d$_6$-DMSO, 100 MHz): δ132.2, 140.3, 136.7, 134.3, 132.9, 132.8, 130.8, 129.7, 128.6, 128.3, 127.8, 127.0, 125.5, 40.0.

Example 7

3-(2,4-dichlorophenylthio)-4-(2,2,2-trifluoro-ethyl)sulphonylamino-benzosulphonamide

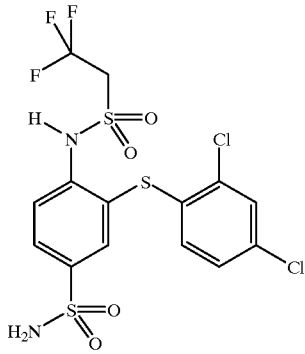

Mp: 210–213° C.

$^{13}$C-NMR (d$_6$-DMSO, 100 MHz): δ143.0, 139.2, 134.7, 133.3, 133.0, 132.3, 130.1, 130.0, 129.8, 128.6, 127.1, 126.7, 123.7, 120.9, 55.45, 55.15, 54.85, 54.55.

Example 8

3-(2,4-dichlorophenylthio)-4-methoxycarbonylmethylsuphonlamino-benzosulphonamide

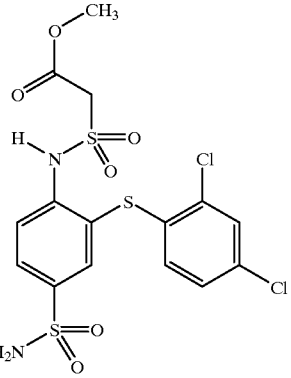

mp: 182–185° C.

$^{13}$C-NMR (d$_6$-DMSO, 100 MHz): δ163.5, 142.4, 140.3, 134.3, 132.9, 132.8, 132.4, 130.8, 129.7, 128.6, 127.1, 125.8, 57.5, 52.8.

EXAMPLE A

Human COX-2 Test

Cells of a human monocytoid cell line were stimulated with lipopolysaccharide (LPS) (incubator at 37° C., 5% CO$_2$-enriched atmosphere and almost 100% atmospheric humidity), in order to induce COX-2. Following this, the culture medium (RPMI 1640, enriched with 10% FCS, 2 mM glutamine, 10000 U/ml penicillin, 10 ng/ml streptomycin and 1 mM pyruvate) is refreshed and potential inhibitor substances of cyclooxygenase-II, dissolved in culture medium or in phosphate-buffered saline or in some other solvent compatible with cell cultures, are added and then incubated for half an hour as described above. Arachidonic acid is added by pipette and incubation is carried out for a further 15 minutes. The culture supernatant of the cells is removed and its content of products of cyclooxygenase metabolism (e.g. Prostaglandin E2, Prostaglandin F$_{1a}$, Thromboxane B$_2$) is measured by ELISA.

EXAMPLE B

Human COX-1 Test

Inhibition of the arachidonic acid-induced aggregation of washed human thrombocytes was used as a test system for an estimation of the inhibition of cyclooxygenase-I. A thrombocyte suspension at 37° C. was added to the test substances 2 minutes before addition of the arachidonic acid (10 μM final concentration) and the aggregation course was recorded via an aggregometer. With the assistance of a concentration-effect curve, the concentration of test substance was determined at which 50% aggregation was measured (IC50).

The results of both tests, and also the selectivity determined from the tests, are given in Table 1.

TABLE 1

| Compound according to Example | COX I IC50 μM | COX II IC50 μM | COX I/COX II |
|---|---|---|---|
| 1 | 25 | 0.10 | 250 |
| 6 | 20 | 0.10 | 200 |

What is claimed is:

1. Compounds of formula I

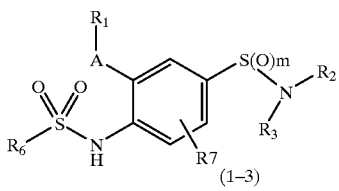

(1-3)

wherein

A denotes oxygen, sulphur or NH, $R^1$ denotes an optionally unsaturated alkyl or alkyloxyalkyl group, optionally mono- or polysubstituted or mixed substituted by halogen, alkoxy, oxo or cyano, a cycloalkyl, aryl or heteroaryl group optionally mono- or polysubstituted or mixed substituted by halogen, alkyl, $CF_3$, cyano or alkoxy, $R_2$ and $R_3$, independently from one another, denote hydrogen, an optionally polyfluorinated alkyl group, an aralkyl, aryl or heteroaryl group or a group $(CH_2)_n$—X, or $R_2$ and $R_3$, together with the N- atom denotes a 3- to 7-membered saturated, partially or completely unsaturated heterocycle with one or more heteroatoms N, O or S, which may optionally be substituted by oxo, an alkyl, alkylaryl or aryl group, or a group $(CH_2)_n$—X, X denotes halogen, $NO_2$, —$OR_4$, —$COR_4$, —$CO_2R_4$, —$OCO_2R_4$, —CN, —$CONR_4OR_5$, —$CONR_4R_5$, $SR_4$, —$S(O)R_4$, —$S(O)_2R_4$, —$NR_4R_5$, —$NCH(O)R_4$, $NHS(O)_2R_4$, n is a whole number from 0 to 6, $R_6$ denotes a straight-chained or branched alkyl group with 1–10 C-atoms, a vinyl group, a cycloalkyl group, an alkylene carboxyl group, an aryl group, aralkyl group, a heteroaryl or beteroaralkyl group, which may optionally be substituted by halogen or alkoxy, $R_7$ denotes hydrogen, halogen, hydroxy, a straight-chained or branched alkyl, alkoxy, acyloxy or alkyloxycarbonyl group with 1–6 C-atoms, which may optionally be mono- or polysubstituted by halogen, —$NO_2$, —$OR_4$, —$COR_4$, —$CO_2R_4$, —$OCO_2R_4$, —CN, —$CONR_4OR_5$, —$CONR_4R_5$, —$SR_4$, —$S(O)R_4$, —$S(O)_2R_4$, —$NR_4R_5$, —$NHC(O)R_4$, —$NHS(O)_2R_4$, or a polyfluoroalkyl group, $R_4$ and $R_5$, independently from one another, denote hydrogen, alkyl, aralkyl or aryl, and m is a whole number from 0 to 2, and the pharmaceutically-acceptable salts thereof.

2. Compounds of formula I according to claim 1, wherein $R_7$ denotes halogen, hydroxy or an alkyl or alkoxycarbonyl group with 1–4 C-atoms which may optionally be substituted by halogen or hydroxy.

3. Compounds of formula I according to claim 1, wherein $R_1$ may optionally be an unsaturated alkyl or alkyloxyalkyl group which may optionally bemono- or polysubstituted or mixed substituted by halogen, alkoxy, oxo or cyano.

4. Compounds of formula I according to claim 2, wherein $R_1$ may optionally be an unsaturated alkyl or alkyloxyalkyl group which may optionally be mono- or polysubstituted or mixed substituted by halogen, alkoxy, oxo or cyano.

5. A pharmaceutical composition containing as an active ingredient at least one compound of formula I according to claim 1.

6. A method of treatment and alleviation of diseases or disorders which can be healed or alleviated by inhibition of the enzyme cyclooxygenase II which comprises administering to a patient in need of same the compound of formula I according to claim 1.

7. A method for treatment or alleviation of inflammatory processes which comprises administering to a patient in need of same the compound of formula I according to claim 1.

8. A method for treatment of pain which comprises administering to a patient in need of same the compound of formula I according to claim 1.

* * * * *